(12) United States Patent　　(10) Patent No.: US 10,433,928 B2
Unger　　(45) Date of Patent: Oct. 8, 2019

(54) MULTIPLE NEEDLE INJECTOR

(71) Applicant: ALLERGAN PHARMACEUTICALS HOLDINGS (IRELAND) UNLIMITED COMPANY, Dublin (IE)

(72) Inventor: Jacob G. Unger, Nashville, TN (US)

(73) Assignee: Allergan Pharmaceuticals Holdings (Ireland) Unlimited Company, Dublin (IE)

( * ) Notice: Subject to any disclaimer, the term of this patent is extended or adjusted under 35 U.S.C. 154(b) by 113 days.

(21) Appl. No.: 15/066,949

(22) Filed: Mar. 10, 2016

(65) Prior Publication Data

US 2016/0263358 A1　Sep. 15, 2016

Related U.S. Application Data

(60) Provisional application No. 62/131,064, filed on Mar. 10, 2015.

(51) Int. Cl.
| | |
|---|---|
| *A61B 90/00* | (2016.01) |
| *A61F 2/12* | (2006.01) |
| *A61M 5/32* | (2006.01) |
| *A61B 17/00* | (2006.01) |

(52) U.S. Cl.
CPC .... *A61B 90/02* (2016.02); *A61B 2017/00796* (2013.01); *A61F 2/12* (2013.01); *A61F 2250/0003* (2013.01); *A61M 5/3298* (2013.01); *A61M 2206/20* (2013.01)

(58) Field of Classification Search
CPC . A61B 90/02; A61B 2017/00796; A61F 2/12; A61F 2250/0003

USPC .................................................. 604/73, 506
See application file for complete search history.

(56) References Cited

U.S. PATENT DOCUMENTS

| | | |
|---|---|---|
| 1,250,114 A | 12/1917 | Bigelow et al. |
| 1,558,037 A | 10/1925 | Morton |
| 1,591,021 A | 7/1926 | Davis |
| 2,007,140 A | 7/1935 | Ragnar |
| 2,302,986 A | 11/1942 | Vollrath |
| 2,491,978 A | 12/1949 | Helfman |
| 2,551,902 A | 5/1951 | Rieck |
| 2,737,946 A | 3/1956 | Hein, Jr. |
| 2,853,070 A | 9/1958 | Julliard |
| 3,086,530 A | 4/1963 | Groom |
| 3,161,323 A | 12/1964 | Bent |

(Continued)

FOREIGN PATENT DOCUMENTS

| | | |
|---|---|---|
| CA | 264261 | 9/1926 |
| CN | 2535071 Y | 2/2003 |

(Continued)

OTHER PUBLICATIONS

PCT/US2016/021838 International Search Report dated May 17, 2016.

(Continued)

*Primary Examiner* — Phillip A Gray
(74) *Attorney, Agent, or Firm* — Nathan S. Smith; Morgan, Lewis & Bockius LLP

(57) ABSTRACT

An improved injector needle apparatus is described with inherent properties for increasing linear flow rates when inserted into a subcutaneous port during tissue expansion thus decreasing procedure time.

29 Claims, 6 Drawing Sheets

(56) References Cited

U.S. PATENT DOCUMENTS

| | | |
|---|---|---|
| D202,754 S | 11/1965 | Fnftolin |
| D214,112 S | 5/1969 | Langdon |
| 3,517,668 A | 6/1970 | Brickson |
| 3,595,231 A | 7/1971 | Pistor |
| D224,066 S | 6/1972 | McDonald |
| 3,720,211 A | 3/1973 | Kyrias |
| 3,767,085 A | 10/1973 | Cannon et al. |
| 3,807,048 A | 4/1974 | Malmin |
| 3,910,282 A | 10/1975 | Messer et al. |
| 3,916,777 A | 11/1975 | Earl |
| 4,064,879 A | 12/1977 | Leibinsohn |
| 4,240,423 A | 12/1980 | Akhavi |
| 4,240,426 A | 12/1980 | Akhavi |
| 4,273,122 A | 6/1981 | Whitney et al. |
| 4,326,517 A | 4/1982 | Whitney et al. |
| 4,346,708 A | 8/1982 | Leeven |
| 4,444,560 A | 4/1984 | Jacklich |
| 4,529,401 A | 7/1985 | Leslie et al. |
| 4,605,691 A | 8/1986 | Balazs et al. |
| 4,617,016 A | 10/1986 | Blomberg |
| 4,624,659 A | 11/1986 | Goldberg |
| 4,627,444 A | 12/1986 | Brooker |
| 4,671,255 A | 6/1987 | Dubrul et al. |
| 4,695,273 A | 9/1987 | Brown |
| 4,699,612 A | 10/1987 | Hamacher |
| 4,710,172 A | 12/1987 | Jacklich |
| 4,719,918 A | 1/1988 | Bonomo et al. |
| 4,755,169 A | 7/1988 | Sarnoff |
| 4,759,750 A | 7/1988 | Devries |
| 4,800,901 A | 1/1989 | Rosenberg |
| 4,832,692 A | 5/1989 | Box |
| 4,841,948 A | 6/1989 | Bauer et al. |
| 4,841,992 A | 6/1989 | Sasaki et al. |
| 4,846,886 A | 7/1989 | Fey et al. |
| D303,010 S | 8/1989 | Jabbusch |
| 4,869,717 A | 9/1989 | Adair |
| 4,898,572 A | 2/1990 | Surugue nee Lasnier |
| 4,908,029 A | 3/1990 | Bark et al. |
| 4,909,932 A | 3/1990 | Monnet |
| 4,955,905 A | 9/1990 | Reed |
| 4,957,744 A | 9/1990 | dellaValle et al. |
| 5,024,613 A | 6/1991 | Vasconcellos |
| 5,024,656 A | 6/1991 | Gasaway et al. |
| 5,046,506 A | 9/1991 | Singer |
| 5,066,303 A | 11/1991 | Bark et al. |
| 5,092,348 A | 3/1992 | Dubrul et al. |
| 5,100,390 A | 3/1992 | Lubeck et al. |
| 5,104,375 A | 3/1992 | Lubeck et al. |
| 5,116,358 A | 5/1992 | Granger et al. |
| 5,127,436 A | 7/1992 | Campion et al. |
| 5,137,181 A | 8/1992 | Keller |
| 5,141,496 A | 8/1992 | Dalto et al. |
| 5,211,644 A | 5/1993 | VanBeek et al. |
| 5,258,013 A | 11/1993 | Granger et al. |
| 5,270,685 A | 12/1993 | Hagen |
| 5,279,544 A | 1/1994 | Gross |
| 5,295,980 A | 3/1994 | Ersek |
| 5,305,788 A | 4/1994 | Mayeux |
| 5,318,544 A | 6/1994 | Drypen |
| 5,322,511 A | 6/1994 | Armbruster et al. |
| 5,344,407 A | 9/1994 | Ryan |
| 5,354,279 A | 10/1994 | Hofling |
| 5,368,572 A | 11/1994 | Shirota |
| 5,383,851 A | 1/1995 | Mackinnon, Jr. |
| 5,405,330 A | 4/1995 | Zunitch et al. |
| 5,433,352 A | 7/1995 | Ronvig |
| 5,478,327 A | 12/1995 | McGregor et al. |
| 5,520,658 A | 5/1996 | Holm |
| 5,540,657 A | 7/1996 | Kurjan |
| 5,549,672 A | 8/1996 | Maddock et al. |
| 5,584,815 A | 12/1996 | Pawelka et al. |
| 5,611,809 A | 3/1997 | Marshall et al. |
| D378,939 S | 4/1997 | Smith et al. |
| 5,650,317 A | 7/1997 | Chang et al. |
| 5,690,618 A | 11/1997 | Smith et al. |
| 5,716,404 A | 2/1998 | Vacanti |
| 5,722,829 A | 3/1998 | Wilcox et al. |
| 5,728,077 A | 3/1998 | Williams |
| 5,752,970 A | 5/1998 | Yoon |
| 5,807,340 A | 9/1998 | Pokras |
| 5,814,511 A | 9/1998 | Chang et al. |
| 5,817,033 A | 10/1998 | DeSantis |
| 5,824,335 A | 10/1998 | Dorigatti et al. |
| 5,846,225 A | 12/1998 | Rosengart et al. |
| 5,853,388 A | 12/1998 | Semel |
| 5,941,845 A | 8/1999 | Tu et al. |
| 5,964,737 A | 10/1999 | Caizza |
| 5,972,385 A | 10/1999 | Liu et al. |
| 6,047,861 A | 4/2000 | Vidal et al. |
| D424,194 S | 5/2000 | Holdaway et al. |
| 6,077,251 A | 6/2000 | Ting et al. |
| 6,082,364 A | 7/2000 | Balian et al. |
| 6,083,912 A | 7/2000 | Khouri |
| 6,102,929 A | 8/2000 | Conway et al. |
| 6,129,761 A | 10/2000 | Hubbell et al. |
| 6,159,233 A | 12/2000 | Matsuzawa |
| 6,171,276 B1 | 1/2001 | Lippe |
| 6,171,610 B1 | 1/2001 | Vacanti et al. |
| 6,176,396 B1 | 1/2001 | Hamada et al. |
| 6,183,434 B1 | 2/2001 | Eppstein |
| D441,077 S | 4/2001 | Garito et al. |
| 6,214,045 B1 | 4/2001 | Corbitt, Jr. et al. |
| 6,231,552 B1 | 5/2001 | Jentzen |
| 6,231,570 B1 | 5/2001 | Tu et al. |
| 6,239,105 B1 | 5/2001 | Brewitt et al. |
| 6,283,951 B1 | 9/2001 | Flaherty et al. |
| 6,293,925 B1 | 9/2001 | Safabash et al. |
| 6,303,518 B1 | 10/2001 | Aceti |
| 6,312,412 B1 | 11/2001 | Saied |
| 6,316,247 B1 | 11/2001 | Katz |
| 6,432,046 B1 | 8/2002 | Yarush et al. |
| 6,451,240 B1 | 9/2002 | Sherman et al. |
| 6,482,187 B1 | 11/2002 | Gibbs |
| 6,488,651 B1 | 12/2002 | Morris |
| 6,551,290 B1 | 4/2003 | Elsberry et al. |
| 6,582,960 B1 | 6/2003 | Martin et al. |
| 6,595,960 B2 | 7/2003 | West et al. |
| 6,607,512 B2 | 8/2003 | Oliver |
| 6,607,513 B1 * | 8/2003 | Down ............... A61M 37/0015 604/239 |
| 6,610,033 B1 | 8/2003 | Melanson et al. |
| 6,611,707 B1 | 8/2003 | Prausnitz et al. |
| 6,613,010 B2 | 9/2003 | Castellano |
| 6,616,448 B2 | 9/2003 | Friedman |
| 6,638,308 B2 | 10/2003 | Corbitt |
| D483,116 S | 12/2003 | Castellano |
| 6,656,488 B2 | 12/2003 | Yi et al. |
| 6,666,893 B2 | 12/2003 | Burg et al. |
| 6,689,095 B1 | 2/2004 | Garitano et al. |
| 6,689,103 B1 | 2/2004 | Palasis |
| 6,716,190 B1 * | 4/2004 | Glines ................ A61M 5/3007 604/141 |
| 6,777,231 B1 | 8/2004 | Katz et al. |
| 6,780,171 B2 | 8/2004 | Gabel |
| 6,783,514 B2 | 8/2004 | Tovey et al. |
| 6,824,526 B2 | 11/2004 | Castellano |
| 6,881,226 B2 | 4/2005 | Corbitt |
| 6,896,666 B2 | 5/2005 | Kochamba |
| 6,901,850 B2 | 6/2005 | Corominas |
| 6,908,453 B2 | 6/2005 | Fleming |
| 6,916,603 B2 | 7/2005 | Baron et al. |
| 6,936,297 B2 | 8/2005 | Roby et al. |
| 6,945,952 B2 | 9/2005 | Kwon |
| 6,991,652 B2 | 1/2006 | Burg et al. |
| 7,004,928 B2 | 2/2006 | Aceti |
| 7,015,037 B1 | 3/2006 | Furcht et al. |
| 7,018,356 B2 | 3/2006 | Wise et al. |
| 7,033,337 B2 | 4/2006 | Hjertman |
| 7,041,088 B2 | 5/2006 | Nawrocki et al. |
| 7,047,070 B2 | 5/2006 | Wilkinson et al. |
| 7,048,729 B2 | 5/2006 | Meglin et al. |
| 7,097,631 B2 | 8/2006 | Trautman |
| 7,108,681 B2 | 9/2006 | Gartstein |
| 7,115,108 B2 | 10/2006 | Wilkinson et al. |

(56) References Cited

U.S. PATENT DOCUMENTS

| | | |
|---|---|---|
| 7,129,209 B2 | 10/2006 | Rhee et al. |
| 7,150,726 B2 | 12/2006 | Dalton |
| 7,285,266 B2 | 10/2007 | Voumakis et al. |
| 7,302,885 B2 | 12/2007 | Townsend |
| 7,316,822 B2 | 1/2008 | Binette et al. |
| 7,361,163 B2 | 4/2008 | Cohen |
| 7,390,484 B2 | 6/2008 | Fraser |
| 7,419,472 B2 | 9/2008 | Hibner et al. |
| 7,442,187 B2 | 10/2008 | Khayal et al. |
| 7,445,793 B2 | 11/2008 | Niwa et al. |
| 7,494,473 B2 | 2/2009 | Eggers et al. |
| 7,501,115 B2 | 3/2009 | Fraser et al. |
| 7,504,386 B2 | 3/2009 | Pressato et al. |
| 7,514,075 B2 | 4/2009 | Hedrick et al. |
| 7,556,615 B2 | 7/2009 | Pettis et al. |
| 7,559,952 B2 | 7/2009 | Pinchuck |
| 7,560,276 B2 | 7/2009 | Harmon et al. |
| 7,588,547 B2 | 9/2009 | Deem |
| 7,611,495 B1 | 11/2009 | Gianturco |
| 7,651,475 B2 | 1/2010 | Angel |
| 7,651,684 B2 | 1/2010 | Hedrick et al. |
| 7,662,110 B2 | 2/2010 | Flaherty |
| 7,664,545 B2 | 2/2010 | Westersten et al. |
| 7,666,339 B2 | 2/2010 | Chaouk et al. |
| D615,192 S | 5/2010 | Mudd et al. |
| 7,722,582 B2 | 5/2010 | Lina et al. |
| 7,762,983 B2 | 7/2010 | Arnissolle |
| 7,767,452 B2 | 8/2010 | Kleinsek et al. |
| 7,799,767 B2 | 9/2010 | Lamberti et al. |
| 7,850,656 B2 | 12/2010 | McKay et al. |
| 7,850,683 B2 | 12/2010 | Elkins |
| 7,875,296 B2 | 1/2011 | Binette et al. |
| 7,878,981 B2 | 2/2011 | Strother et al. |
| 7,896,837 B2 | 3/2011 | Wilkinson et al. |
| D637,287 S | 5/2011 | Mudd et al. |
| 7,998,170 B2 | 8/2011 | Cunningham |
| 8,012,139 B2 | 9/2011 | McKay et al. |
| 8,029,460 B2 | 10/2011 | Rush et al. |
| 8,053,423 B2 | 11/2011 | Lamberti et al. |
| 8,066,629 B2 | 11/2011 | Dlugos |
| 8,066,691 B2 | 11/2011 | Khouri |
| 8,083,722 B2 | 12/2011 | McKay |
| 8,088,108 B2 * | 1/2012 | Kraft ............... A61M 37/0015 604/173 |
| 8,137,705 B2 | 3/2012 | Doyle et al. |
| 8,153,591 B2 | 4/2012 | Masters et al. |
| 8,157,830 B2 | 4/2012 | Wenchell |
| 8,172,815 B2 | 5/2012 | Down et al. |
| 8,216,190 B2 | 7/2012 | Gartstein |
| 8,236,021 B2 | 8/2012 | Kluge |
| 8,291,768 B2 | 10/2012 | Spiegel |
| 8,303,518 B2 | 11/2012 | Aceti |
| 8,303,545 B2 | 11/2012 | Schraga |
| 8,343,132 B2 | 1/2013 | Heneveld et al. |
| 8,349,554 B2 | 1/2013 | Bahrami et al. |
| 8,353,871 B2 | 1/2013 | Zimmerman |
| 8,366,643 B2 | 2/2013 | Deem |
| 8,394,118 B2 | 3/2013 | Jones et al. |
| 8,409,147 B2 | 4/2013 | Kraft |
| 8,409,185 B2 | 4/2013 | Burger |
| 8,480,630 B2 | 7/2013 | Mudd et al. |
| 8,535,278 B2 | 9/2013 | Mudd et al. |
| 8,562,571 B2 | 10/2013 | Mudd et al. |
| 8,603,028 B2 | 12/2013 | Mudd et al. |
| 8,632,501 B2 | 1/2014 | Kraft |
| 8,636,797 B2 | 1/2014 | Chitre et al. |
| 8,657,786 B2 | 2/2014 | Bahrami et al. |
| 8,668,675 B2 | 3/2014 | Chase |
| 8,708,965 B2 | 4/2014 | Boyden et al. |
| 8,712,815 B1 | 4/2014 | Nichols et al. |
| 8,821,446 B2 | 9/2014 | Trautman |
| 8,900,181 B2 | 12/2014 | Knowlton |
| 8,900,186 B2 | 12/2014 | Pettis et al. |
| 8,945,060 B2 | 2/2015 | Bunch |
| 9,017,289 B2 | 4/2015 | Backes |
| 9,017,318 B2 | 4/2015 | Fourkas |
| 9,039,688 B2 | 5/2015 | Palmer, III |
| 9,066,712 B2 | 6/2015 | Fourkas |
| 9,072,498 B2 | 7/2015 | Elkins |
| 9,101,346 B2 | 8/2015 | Burger |
| 9,113,855 B2 | 8/2015 | Burger |
| 9,149,331 B2 | 10/2015 | Deem |
| 9,155,584 B2 | 10/2015 | Fourkas |
| 9,180,273 B2 | 11/2015 | Konstantino |
| 9,214,030 B2 | 12/2015 | Sole et al. |
| 9,227,023 B2 | 1/2016 | Kraft |
| 9,241,753 B2 | 1/2016 | Fourkas |
| 9,254,162 B2 | 2/2016 | Burger |
| 9,289,605 B2 | 3/2016 | Choi |
| 9,314,568 B2 | 4/2016 | Gurtner et al. |
| 9,468,748 B2 | 10/2016 | Bang |
| 2001/0008937 A1 | 7/2001 | Callegaro et al. |
| 2002/0010433 A1 | 1/2002 | Johnson |
| 2002/0026039 A1 | 2/2002 | Bellini et al. |
| 2002/0065483 A1 | 5/2002 | Leon |
| 2002/0133114 A1 | 9/2002 | Itoh |
| 2002/0151843 A1 | 10/2002 | Correa et al. |
| 2003/0028154 A1 | 2/2003 | Ross |
| 2003/0050602 A1 | 3/2003 | Pettis et al. |
| 2003/0078912 A1 | 4/2003 | Oliver |
| 2003/0144632 A1 | 7/2003 | Hommann et al. |
| 2003/0181863 A1 | 9/2003 | Ackley |
| 2003/0199883 A1 | 10/2003 | Laks |
| 2003/0233067 A1 | 12/2003 | McIntosh et al. |
| 2004/0010224 A1 | 1/2004 | Bodmeier |
| 2004/0015133 A1 | 1/2004 | Karim |
| 2004/0092011 A1 | 5/2004 | Wilkison et al. |
| 2004/0092927 A1 | 5/2004 | Podhajsky et al. |
| 2004/0147883 A1 | 7/2004 | Tsai |
| 2004/0192643 A1 | 9/2004 | Pressato et al. |
| 2004/0220532 A1 | 11/2004 | Caizza |
| 2005/0025755 A1 | 2/2005 | Hedrick |
| 2005/0033362 A1 | 2/2005 | Grafton |
| 2005/0085767 A1 | 4/2005 | Menassa |
| 2005/0123895 A1 | 6/2005 | Freund |
| 2005/0131353 A1 | 6/2005 | Mossanen-Shams et al. |
| 2005/0137496 A1 | 7/2005 | Walsh et al. |
| 2005/0147562 A1 | 8/2005 | Hunter et al. |
| 2005/0177117 A1 | 8/2005 | Crocker et al. |
| 2005/0182446 A1 | 8/2005 | DeSantis |
| 2005/0215956 A1 | 9/2005 | Nerney |
| 2005/0261633 A1 | 11/2005 | Khalaj |
| 2006/0041320 A1 | 2/2006 | Matsuda |
| 2006/0079765 A1 | 4/2006 | Neer |
| 2006/0089594 A1 | 4/2006 | Landau |
| 2006/0150742 A1 | 7/2006 | Esnouf |
| 2007/0038181 A1 | 2/2007 | Melamud |
| 2007/0083155 A1 | 4/2007 | Muller |
| 2007/0085767 A1 | 4/2007 | Jung et al. |
| 2007/0100363 A1 | 5/2007 | Dollar et al. |
| 2007/0167920 A1 | 7/2007 | Hommann |
| 2007/0191781 A1 | 8/2007 | Richards et al. |
| 2007/0212385 A1 | 9/2007 | David |
| 2007/0250010 A1 | 10/2007 | Hohlfelder et al. |
| 2007/0251531 A1 | 11/2007 | Khouri |
| 2007/0270710 A1 | 11/2007 | Frass et al. |
| 2008/0015522 A1 | 1/2008 | Yeshurun |
| 2008/0033347 A1 | 2/2008 | D'Arrigo et al. |
| 2008/0058706 A1 | 3/2008 | Zhang |
| 2008/0058839 A1 | 3/2008 | Nobles |
| 2008/0071385 A1 | 3/2008 | Binette et al. |
| 2008/0097325 A1 | 4/2008 | Tanaka et al. |
| 2008/0108952 A1 | 5/2008 | Horvath et al. |
| 2008/0114305 A1 | 5/2008 | Gerondale |
| 2008/0119797 A1 | 5/2008 | Kim |
| 2008/0119876 A1 | 5/2008 | Price et al. |
| 2008/0161772 A1 | 7/2008 | Nayak |
| 2008/0167674 A1 | 7/2008 | Bodduluri et al. |
| 2008/0188816 A1 | 8/2008 | Shimazaki |
| 2008/0200758 A1 | 8/2008 | Orbay et al. |
| 2008/0243028 A1 | 10/2008 | Howard et al. |
| 2008/0281278 A1 | 11/2008 | Williams |
| 2008/0299213 A2 | 12/2008 | Kleinsek |
| 2008/0317718 A1 | 12/2008 | Yoshimura |

(56) References Cited

U.S. PATENT DOCUMENTS

| | | |
|---|---|---|
| 2009/0088703 A1 | 4/2009 | Azar |
| 2009/0098177 A1 | 4/2009 | Werkmeister et al. |
| 2009/0123547 A1 | 5/2009 | Hill |
| 2009/0124552 A1 | 5/2009 | Hill |
| 2009/0124996 A1 | 5/2009 | Heneveld et al. |
| 2009/0125050 A1 | 5/2009 | Dixon |
| 2009/0131886 A1 | 5/2009 | Liu et al. |
| 2009/0143746 A1 | 6/2009 | Mudd et al. |
| 2009/0162415 A1 | 6/2009 | Huang et al. |
| 2009/0187118 A1 | 7/2009 | Kim et al. |
| 2009/0234322 A1 | 9/2009 | Fischer |
| 2009/0240200 A1 | 9/2009 | Heneveld et al. |
| 2009/0246182 A1 | 10/2009 | Casteilla |
| 2009/0247953 A1 | 10/2009 | Yeshurun |
| 2009/0259180 A1 | 10/2009 | Choi |
| 2009/0275917 A1 | 11/2009 | Azar |
| 2009/0287161 A1 | 11/2009 | Traub |
| 2009/0299328 A1 | 12/2009 | Mudd et al. |
| 2009/0312746 A1 | 12/2009 | Khouri |
| 2009/0317367 A1 | 12/2009 | Chazenbalk |
| 2010/0006095 A1 | 1/2010 | Woodcock |
| 2010/0010627 A1 | 1/2010 | Matheny |
| 2010/0030152 A1 | 2/2010 | Lee et al. |
| 2010/0069848 A1 | 3/2010 | Alferness |
| 2010/0100114 A1 | 4/2010 | Berger |
| 2010/0121307 A1 | 5/2010 | Lockard |
| 2010/0152675 A1 | 6/2010 | McClintock |
| 2010/0152679 A1 | 6/2010 | Tezel |
| 2010/0179488 A1 | 7/2010 | Spiegel |
| 2010/0256594 A1 | 10/2010 | Kimmell et al. |
| 2010/0256596 A1 | 10/2010 | Chomas |
| 2010/0279405 A1 | 11/2010 | Peterson |
| 2010/0280488 A1 | 11/2010 | Pruiitt et al. |
| 2010/0282774 A1 | 11/2010 | Greter et al. |
| 2010/0286618 A1* | 11/2010 | Choi ............... A61M 5/32 604/173 |
| 2011/0009808 A1 | 1/2011 | AlGhamdi |
| 2011/0021905 A1 | 1/2011 | Patrick et al. |
| 2011/0028910 A1 | 2/2011 | Weber |
| 2011/0070281 A1 | 3/2011 | Altman et al. |
| 2011/0092916 A1 | 4/2011 | Tezel et al. |
| 2011/0137286 A1 | 6/2011 | Mudd et al. |
| 2011/0150823 A1 | 6/2011 | Huang |
| 2011/0152926 A1 | 6/2011 | Vetrecin |
| 2011/0160674 A1 | 6/2011 | Holmes et al. |
| 2011/0172645 A1 | 7/2011 | Moga |
| 2011/0190974 A1 | 8/2011 | Holmes et al. |
| 2011/0202014 A1 | 8/2011 | Mutzbauer |
| 2011/0213336 A1 | 9/2011 | Cucin |
| 2011/0218494 A1 | 9/2011 | Assaf |
| 2011/0218497 A1 | 9/2011 | Assaf |
| 2011/0230839 A1 | 9/2011 | Bahrami et al. |
| 2011/0238038 A1 | 9/2011 | Sefi |
| 2011/0263724 A1 | 10/2011 | Gurtner |
| 2011/0282324 A1 | 11/2011 | Kurokawa et al. |
| 2011/0282381 A1 | 11/2011 | Cronin et al. |
| 2011/0319865 A1 | 12/2011 | Buss |
| 2012/0010146 A1 | 1/2012 | Han et al. |
| 2012/0041374 A1 | 2/2012 | Lee |
| 2012/0076868 A1 | 3/2012 | Lamberti et al. |
| 2012/0089211 A1 | 4/2012 | Curtis |
| 2012/0101475 A1 | 4/2012 | Wilmot |
| 2012/0123194 A1 | 5/2012 | Beckman |
| 2012/0123537 A1 | 5/2012 | Manesis et al. |
| 2012/0141532 A1 | 6/2012 | Blanda et al. |
| 2012/0150266 A1 | 6/2012 | Shalev |
| 2012/0156265 A1 | 6/2012 | Binette et al. |
| 2012/0209248 A1 | 8/2012 | Gurtner et al. |
| 2012/0245629 A1 | 9/2012 | Gross et al. |
| 2012/0259322 A1 | 10/2012 | Fourkas |
| 2012/0265064 A1 | 10/2012 | Bahrami et al. |
| 2012/0265171 A1 | 10/2012 | Thorne |
| 2012/0296206 A1 | 11/2012 | Bahrami et al. |
| 2013/0012865 A1 | 1/2013 | Sallberg et al. |
| 2013/0041346 A1 | 2/2013 | Alon |
| 2013/0096531 A1 | 4/2013 | Estepa et al. |
| 2013/0122068 A1 | 5/2013 | Fermanian et al. |
| 2013/0131632 A1 | 5/2013 | Mudd et al. |
| 2013/0131633 A1 | 5/2013 | Mudd et al. |
| 2013/0150826 A1 | 6/2013 | Almohizea |
| 2013/0184648 A1 | 7/2013 | Inou et al. |
| 2013/0184696 A1 | 7/2013 | Fourkas |
| 2013/0197446 A1 | 8/2013 | Gustafsson |
| 2013/0197449 A1 | 8/2013 | Franklin et al. |
| 2013/0211374 A1 | 8/2013 | Hetherington |
| 2013/0253289 A1 | 9/2013 | Hadvary |
| 2013/0274655 A1 | 10/2013 | Jennings |
| 2013/0274670 A1 | 10/2013 | Mudd et al. |
| 2013/0280755 A1 | 10/2013 | Hubert |
| 2013/0310763 A1 | 11/2013 | Mudd et al. |
| 2014/0018770 A1 | 1/2014 | Sutkin |
| 2014/0018835 A1 | 1/2014 | Scherkowski |
| 2014/0066845 A1 | 3/2014 | Mudd et al. |
| 2014/0088502 A1 | 3/2014 | Matheny et al. |
| 2014/0088553 A1 | 3/2014 | Hetherington |
| 2014/0114279 A1 | 4/2014 | Klinghoffer |
| 2014/0121587 A1 | 5/2014 | Sallberg et al. |
| 2014/0128685 A1 | 5/2014 | Na |
| 2014/0128810 A1 | 5/2014 | Ozawa et al. |
| 2014/0162901 A1 | 6/2014 | Bahrami et al. |
| 2014/0170299 A1 | 6/2014 | Gill |
| 2014/0228950 A1 | 8/2014 | Whitcup et al. |
| 2014/0228971 A1 | 8/2014 | Kim |
| 2014/0249504 A1 | 9/2014 | Franklin et al. |
| 2014/0257179 A1 | 9/2014 | Schwab et al. |
| 2014/0257190 A1 | 9/2014 | Yue et al. |
| 2014/0309590 A1 | 10/2014 | Bahrami et al. |
| 2014/0343481 A1 | 11/2014 | Ignon |
| 2014/0350514 A1 | 11/2014 | Levin |
| 2014/0350516 A1 | 11/2014 | Schwab |
| 2014/0350517 A1 | 11/2014 | Dominguez |
| 2014/0350518 A1 | 11/2014 | Franklin et al. |
| 2014/0350536 A1 | 11/2014 | Allison |
| 2015/0025459 A1 | 1/2015 | Kimmel et al. |
| 2015/0025563 A1 | 1/2015 | Mosharrafa et al. |
| 2015/0119875 A1 | 4/2015 | Fischell et al. |
| 2015/0126929 A1 | 5/2015 | Franklin et al. |
| 2015/0141956 A1 | 5/2015 | Hoffman et al. |
| 2015/0157809 A1 | 6/2015 | Park et al. |
| 2015/0209265 A1 | 7/2015 | Horne |
| 2015/0343147 A1 | 12/2015 | Franklin et al. |
| 2016/0007990 A1 | 1/2016 | Solish et al. |
| 2016/0058488 A1 | 3/2016 | Fourkas |
| 2016/0095984 A1 | 4/2016 | Franklin et al. |
| 2016/0114144 A1 | 4/2016 | Sumida |
| 2016/0144125 A1 | 5/2016 | Franklin |
| 2016/0207253 A9 | 7/2016 | Down et al. |
| 2016/0213854 A1 | 7/2016 | Schwab et al. |
| 2016/0303314 A1 | 10/2016 | Momose |
| 2017/0080154 A1 | 3/2017 | Mudd et al. |
| 2017/0290987 A1 | 10/2017 | Mandaroux et al. |

FOREIGN PATENT DOCUMENTS

| | | |
|---|---|---|
| CN | 200960353 Y | 10/2007 |
| EP | 0362484 | 4/1990 |
| EP | 0205915 B1 | 7/1990 |
| EP | 0167662 B1 | 12/1990 |
| EP | 0648474 | 4/1995 |
| EP | 0809968 | 12/1997 |
| EP | 1051988 | 11/2000 |
| EP | 1476202 | 11/2004 |
| EP | 1486218 | 12/2004 |
| EP | 1395320 | 6/2006 |
| EP | 1859827 | 11/2007 |
| EP | 1923086 | 5/2008 |
| EP | 2189173 | 5/2010 |
| EP | 2242525 A1 | 10/2010 |
| EP | 2335755 | 6/2011 |
| EP | 2422832 | 2/2012 |
| EP | 2103262 | 2/2013 |
| EP | 2184016 | 4/2013 |
| EP | 2671516 | 12/2013 |
| FR | 53011 | 9/1945 |

(56) References Cited

FOREIGN PATENT DOCUMENTS

| | | |
|---|---|---|
| FR | 2622457 | 5/1989 |
| FR | 2857654 | 1/2005 |
| GB | 2336783 | 5/2003 |
| KR | 20120007473 | 1/2012 |
| KR | 101246570 | 3/2013 |
| KR | 20130036921 | 4/2013 |
| KR | 20130130436 | 12/2013 |
| KR | 20130132196 | 12/2013 |
| KR | 20140029007 | 3/2014 |
| RU | 2286803 | 11/2006 |
| WO | WO 90/001349 | 2/1990 |
| WO | WO 92/013579 | 8/1992 |
| WO | WO 94/012228 | 6/1994 |
| WO | WO 96/025965 | 8/1996 |
| WO | 1997028840 A1 | 8/1997 |
| WO | WO 99/048601 | 9/1999 |
| WO | WO 01/00190 | 1/2001 |
| WO | WO 02/055135 | 7/2002 |
| WO | WO 2004/022603 | 3/2004 |
| WO | WO 2005/095225 | 10/2005 |
| WO | WO 2006/065837 | 6/2006 |
| WO | WO 2008/086479 | 8/2006 |
| WO | 2006118804 A1 | 11/2006 |
| WO | WO 2006/133111 | 12/2006 |
| WO | WO 2007/092929 | 8/2007 |
| WO | WO 2007/095922 | 8/2007 |
| WO | WO 2007/124478 | 11/2007 |
| WO | 2007140381 A2 | 12/2007 |
| WO | WO 2008/019265 | 2/2008 |
| WO | WO 2008/053481 | 5/2008 |
| WO | WO 2008/063569 | 5/2008 |
| WO | WO 2008/072229 | 6/2008 |
| WO | WO 2008/079824 | 7/2008 |
| WO | WO 2008/148026 | 12/2008 |
| WO | WO 2008/148071 | 12/2008 |
| WO | WO 2009/003135 | 12/2008 |
| WO | 2009035680 A1 | 3/2009 |
| WO | WO 2009/047346 | 4/2009 |
| WO | 2009091099 A1 | 7/2009 |
| WO | WO 2009/085548 | 7/2009 |
| WO | WO 2009/098666 | 8/2009 |
| WO | WO 2009/103818 | 8/2009 |
| WO | WO 2009/115581 | 9/2009 |
| WO | WO 2009/155583 | 12/2009 |
| WO | WO 2009/158145 | 12/2009 |
| WO | WO 2010/026299 | 3/2010 |
| WO | WO 2010/028025 | 3/2010 |
| WO | WO 2010/127310 | 11/2010 |
| WO | 2011016785 A1 | 2/2011 |
| WO | 2011073796 A2 | 6/2011 |
| WO | 2011075731 A2 | 6/2011 |
| WO | WO 2011/072399 | 6/2011 |
| WO | WO 2011/109129 | 9/2011 |
| WO | WO 2011/109130 | 9/2011 |
| WO | WO 2012/006587 | 1/2012 |
| WO | WO 2012/019103 | 2/2012 |
| WO | WO 2012/054301 | 4/2012 |
| WO | WO 2012/054311 | 4/2012 |
| WO | 2012127856 A1 | 9/2012 |
| WO | 2012172424 A1 | 12/2012 |
| WO | WO 2013/005881 | 1/2013 |
| WO | WO 2013/054165 | 4/2013 |
| WO | WO 2013/055832 | 4/2013 |
| WO | WO 2013/082112 | 6/2013 |
| WO | WO 2013/106857 | 8/2013 |
| WO | WO 2014/026044 | 2/2014 |
| WO | 2014034032 A1 | 3/2014 |
| WO | 2014064534 A3 | 5/2014 |
| WO | WO 2012/174464 | 5/2014 |
| WO | 2014189161 A1 | 11/2014 |
| WO | 2015007243 A1 | 1/2015 |
| WO | WO 2015/020982 | 2/2015 |
| WO | 2013065235 A1 | 4/2015 |
| WO | 2015064031 A1 | 5/2015 |
| WO | WO 2015/105269 | 7/2015 |
| WO | 2015127339 A1 | 8/2015 |
| WO | WO 2015/149031 | 10/2015 |
| WO | 2016008845 A1 | 1/2016 |
| WO | WO 2016/022865 | 2/2016 |
| WO | WO 2016/033584 | 3/2016 |
| WO | WO 2016/033586 | 3/2016 |

OTHER PUBLICATIONS

Hamza, F., et al., A new external filling device in tissue expansion, Plastic and Reconstructive Surgery, Mar. 1998, 813-815, vol. 101, No. 3.

Indian Patent Application No. 190/CHE/2002, Filed Mar. 20, 2002, Published Feb. 3, 2006, Hindustan Latex Limited, Title: A Subcutaneous Tissue Expander.

Indian Patent Application No. 190/CHE/2002, Filing Date: Mar. 20, 2002, Publication Date: Feb. 3, 2006, Applicant: Hindustan Latex Limited (IN).

Indian Patent Specification, Patent No. 209387, Application No. 190/MAS/2002, Filing date: Mar. 20, 2002, Publication Date: Feb. 3, 2006, Date of Grant: Sep. 21, 2007, Applicant: Hindustan Latex Limited (IN).

Bleyer, "SIS Facial Implant 510(k) Summary," Cook Biotech Inc. May 2005.

Davidenko et al., "Collagen-hyaluronic acid scaffolds for adipose tissue engineering", ACTA Biomaterialia, vol. 6, No. 10, Oct. 1, 2010, pp. 3957-3968.

Galderma, "Restylane Smart Click System Injection Device," Mar. 2015, retrieved from http://www.red-dot-21.com/products/restylane-smart-click-system-injection-device-22169.

Galderma, "New Restylane Skinboosters SmartClick delivery system wins prestigious Red Dot design award," Jul. 4, 2014, retrieved from http://www.galderma.com/News/articleType/ArticleView/articleId/64/New-Restylane-Skinboosters-SmartClick-delivery-system-wins-prestigious-Red-Dot-design-award.

ISRWO from PCT/US2009/045831, dated Feb. 24, 2010.

ISRWO from PCT/US2014/039265.

ISRWO from PCT/US2014/039266.

Kilroy et al., "Cytokine Profile of Human Adipose-Derived Stem Cells: Expression of Angiogenic, Hematopoietic, and Pro-Inflammatory Factors," J. Cell. Physiol., 2007, 702-709.

Park et al., "Biological characterization of EDC-crosslinked collagen-hyaluronic acid matrix in dermal tissue restoration", Biomaterials, Elsevier Science Publishers BV, vol. 24, No. 9, Apr. 1, 2003, pp. 1631-1641.

PRIME Journal, "Galderma to launch two new syringes at AMWC 2014," Mar. 2014.

Rehman et al., "Secretion of Angiogenic and Antiapoptotic Factors by Human Adipose Stromal Cells," Circulation, 2004, 1292-1298, 109.

Turtlepin, "The Painless Direct Dermal Injector" Product Information, JM Biotech Co Ltd, 2013.

Wang et al., "In vivo stimulation of de novo collagen production caused by cross-linked hyaluronic acid dermal filler injections in photodamaged human skin.", Archives of Dermatology, American Medical Association, US, vol. 143, No. 2, Feb. 1, 2007, pp. 155-163.

Yoshimura et al., "Cell-Assisted Lipotransfer for Cosmetic Breast Augmentation: Supportive Use of Adipose-Derived Stem/Stromal Cells," Aesth. Plast. Surg., 2008, 48-55.

Yoshimura et al., "Cell-Assisted Lipotransfer for Facial Lipoatrophy: Effects of Clinical Use of Adipose-Derived Stem Cells," Dermatol. Surg., 2008, 1178-1185.

Yoshimura et al., "Characterization of Freshly Isolated and Cultured Cells Derived From the Fatty and Fluid Portions of Liposuction Aspirates," J Cell Physiol, 2006, 1011-1041.

\* cited by examiner

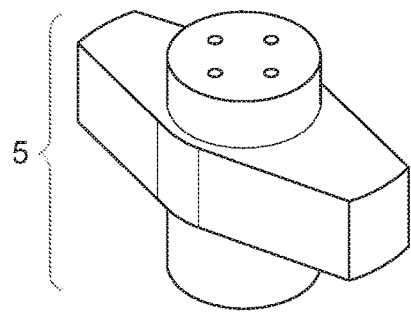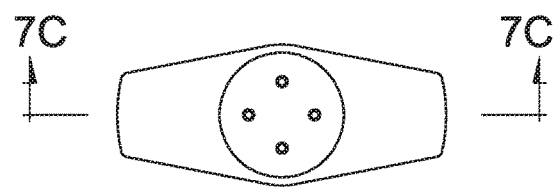
FIG. 7A  FIG. 7B
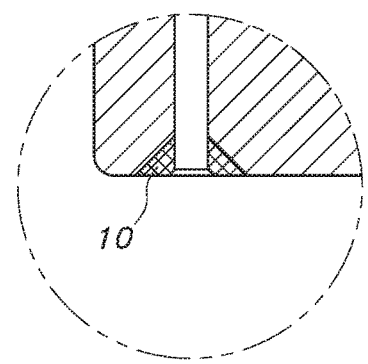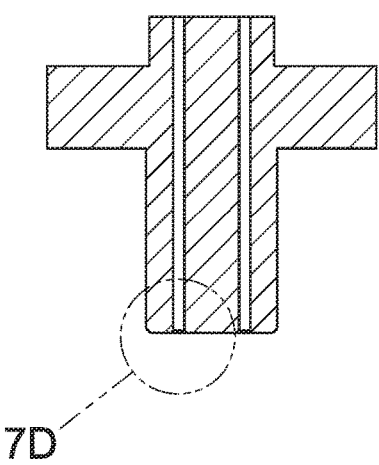
FIG. 7D  FIG. 7C

MULTIPLE NEEDLE INJECTOR

CROSS-REFERENCES TO RELATED APPLICATIONS

This application claims the benefit of U.S. Provisional Application No. 62/131,064, filed Mar. 10, 2015, which is incorporated herein by reference in its entirety.

FIELD OF THE INVENTION

The present invention is generally directed to an apparatus using a plurality of needles to increase flow rates during tissue expansion and injection of fluids into subcutaneous tissue and the method thereof.

BACKGROUND OF THE INVENTION

Breast reconstruction is one of the most common procedures performed in plastic surgery today. One out of eight women will have breast cancer in their lifetime, the majority of whom will undergo reconstruction. Currently federal law mandates that any woman who has breast cancer must be offered reconstruction. Last year 96,000 breast reconstructions were performed, the vast majority of which were expander implant based reconstructions. Of note, many cases are bilateral, and therefore over 100,000 expanders are being utilized in breast reconstruction ever year.

The typical breast reconstruction process involves placing a deflated tissue expander in the chest pocket after mastectomy (breast removal). The expander includes a port through which sterile saline can be forced, causing the volume of the expander to increase. The expander is usually filled with sterile saline in the operating room prior to closing the surgical opening in the skin. The patient then returns to the clinic two weeks later for further expansion. Because the port is covered by skin, the port is located with the aid of a port locator magnet. Once it is located, a needle is placed through the skin into the port and sterile saline is injected. This procedure is done on a weekly basis until the skin envelope is expanded to a large enough size to accommodate the desired implant size for an appropriately sized breast mound. Typically, the expansion procedure is performed four to eight separate times prior to being ready for the expander/implant exchange.

This procedure is not limited to breast reconstruction. Tissue expanders are also used in burn reconstruction and various other types of reconstruction where skin expansion is needed.

The most pressing issue associated with breast and other types of tissue expansion is the exceedingly narrow needle used in current systems, such as the MENTOR brand winged infusion set, as compared to the pipe diameter of the rest of the system. The entire system is bottlenecked by the 21 gauge needle that is used to inject the port. The inner diameter of the needle is 0.51 mm (outer diameter 0.81 mm), which is the maximum allowable gauge needle per the manufacturer instructions (see Mentors Product Website) due to the nature of the port. Narrow needles result in slow flow of sterile saline, and require more time to fill the tissue expander. The filling process in the operating room can be as long as 10 to 15 minutes during which time the surgeons and nurse must patiently wait for the expander to fill with the patient still open. Simply a larger needle would core out the silicone and make the port leak, and thus fail.

SUMMARY OF THE INVENTION

We disclose herein a fluid injector apparatus for injecting fluid through a plurality of needles into a subcutaneous port during tissue expansion comprising a base, tubing connecting the needles, and a base fluid injection system to increase linear flow velocity and decrease procedure time.

We also disclose a method of injecting fluid through a plurality of needles into a subcutaneous port during tissue expansion comprising a base, tubing connecting the needles, and a base fluid injection system to increase linear flow velocity and decrease procedure time.

BRIEF DESCRIPTION OF THE DRAWINGS

Further advantages of the invention will become apparent by reference to the detailed description of preferred embodiments when considered in conjunction with the drawings:

FIG. 6A is a perspective view of the hub of the apparatus. FIG. 6B is a cross-sectional view of the multiple injector needle apparatus. FIG. 6C is a top plan view of the hub of the apparatus. FIG. 6D is a cross sectional view of the hub of the apparatus taken along the line 6D-6D of FIG. 6B.

FIG. 7A-7D are views of an embodiment of the multiple injector needle apparatus. Independently, FIG. 7A is a perspective view of the hub of the apparatus. FIG. 7B is a top plan view of the hub of the apparatus. FIG. 7C is a cross-sectional view of the aggregating cone of the apparatus taken along the line 7C-7C of FIG. 7B, FIG. 7D is a cross-sectional view of the aggregating cone of FIG. 7C of the apparatus at increased magnification.

FIG. 8A is a perspective view of the hub of the apparatus. FIG. 8B is a right side view of the hub of the apparatus. FIG. 8C is a cross-sectional view of the needles and hub of the apparatus.

FIG. 9A is a perspective view of the hub of the apparatus. FIG. 9B is a right side view of the hub of the apparatus. FIG. 9C is a cross-sectional view of the aggregating cone of the apparatus.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

To overcome the issue of the slow flow through a single injection needle, our invention uses a plurality of needles. The typical injection port is nearly 3 cm in diameter. So, while a large single needle would cause failure, multiple small needles can easily be placed into the silicone dome at the same time without breaking the seal. The present invention (as pictured in FIG. 2) would solve the exceedingly small needle issue by allowing for a four (4) times increase in the flow velocity as compared to the current standard and sole existing option by allowing a plurality of separate needles contained within one construct at the end of butterfly tubing thus resulting in immense time savings in the operating room as well as the clinic.

We disclose herein such an apparatus that allows for increased flow rate of fluids into a tissue expander. The apparatus has multiple needles that can be simultaneously inserted into the port, thus allowing more fluid to flow into the expander. As a result of the increased flow, the time to fill the tissue expander is significantly reduced.

Figure 2:
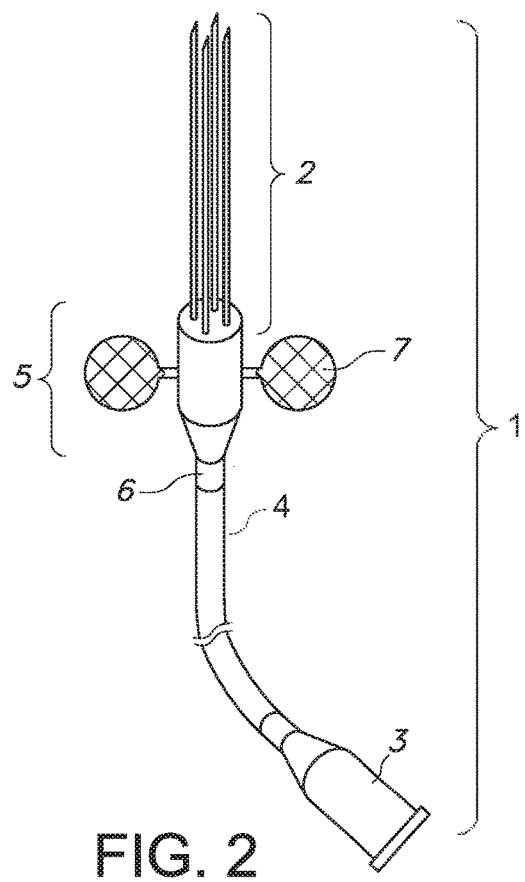
FIG. 2 is a front view of the multiple injector needle apparatus.
Figure 5:
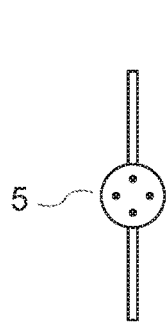
FIG. 5 is a top plan view of the multiple injector needle apparatus.

Referring to the drawings, FIG. 2 illustrates the multiple needle apparatus 1 consisting primarily of needles 2 projecting outward from a hub 5 and tubing 4 for connecting the hub to a fluid source.

Figure 1:
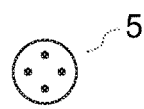
FIG. 1 is a top plan view of the multiple injector needle apparatus.
Figure 4:
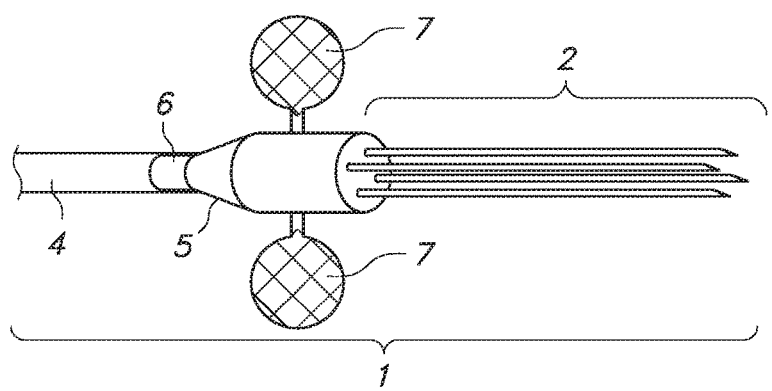
FIG. 4 is a perspective view of the multiple injector needle apparatus.

The needles 2 project from the first end (injection side) of the hub 5 such that they are substantially parallel to each other. As shown in FIG. 1 and FIG. 4, the needles are spaced such that all of them can simultaneously enter the injection port on the breast tissue expander. In the example shown, the needles are spaced no more than five (5) millimeters across. The needles 2 may be shorter than currently used needles, or they may have ultra-thin walls, thus reducing the pressure required for increased flow of fluid into the tissue expander. Any type and sized of needle that allows the flow of liquid may be used in the device, although in a preferred embodiment, a standard hypodermic will be used in the apparatus 1.

Figure 8A:
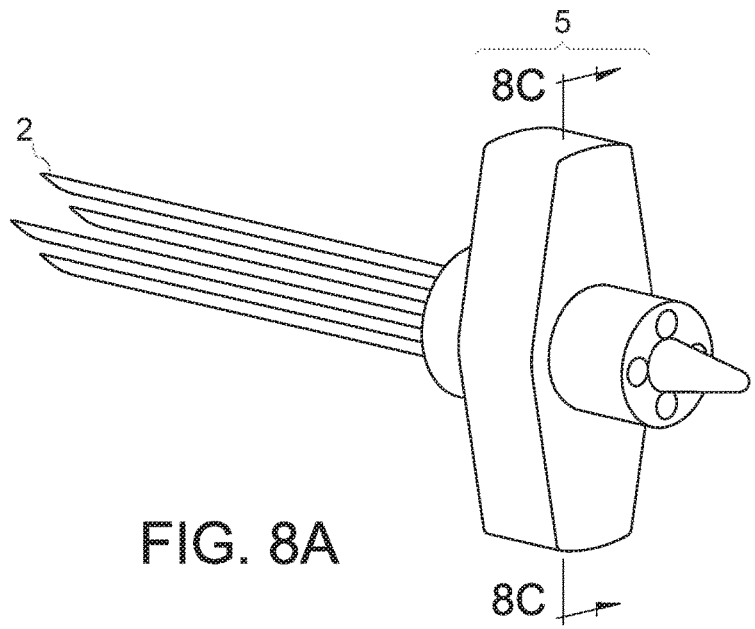
FIG. 8A-8C are views of an embodiment of the apparatus with needles inserted into the hub. Independently.
Figure 8B:
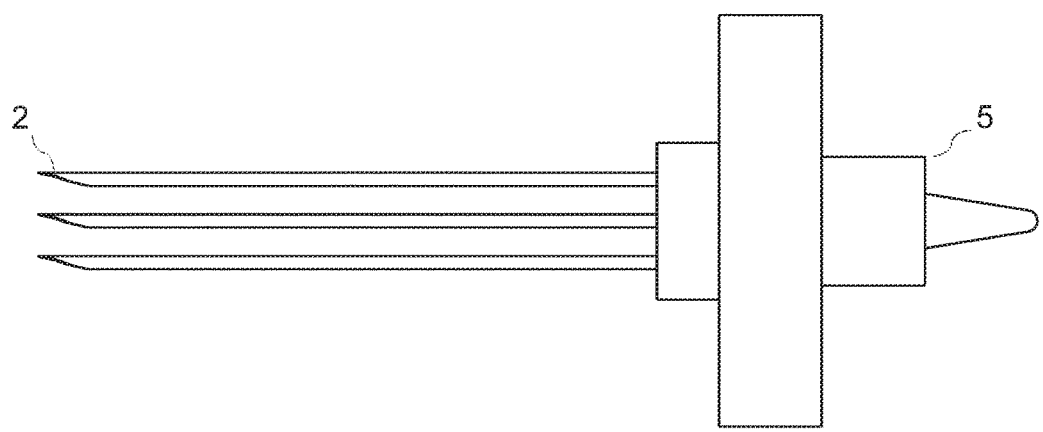
Figure 8C:
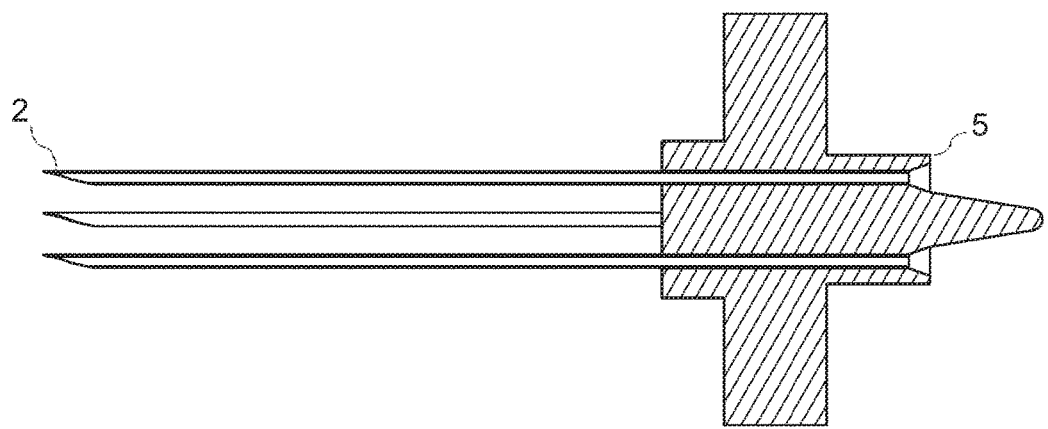
Figure 9A:
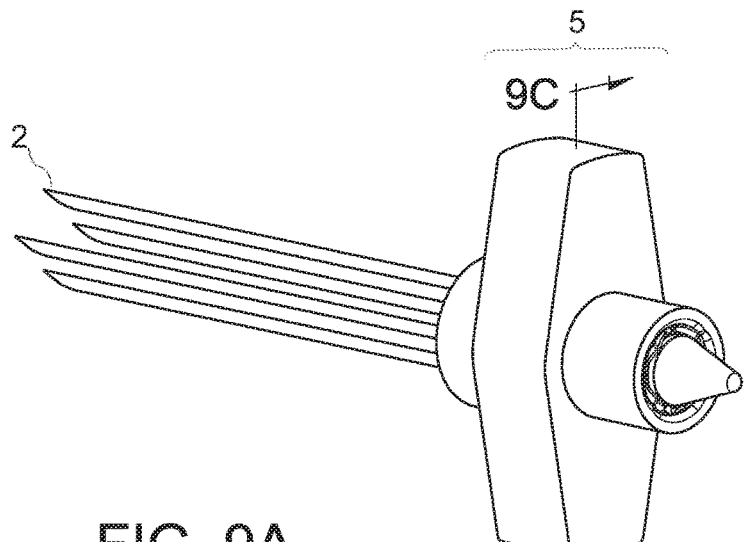
FIG. 9A-9C are views of an embodiment of the apparatus with needles inserted into the hub. Independently.
Figure 9B:
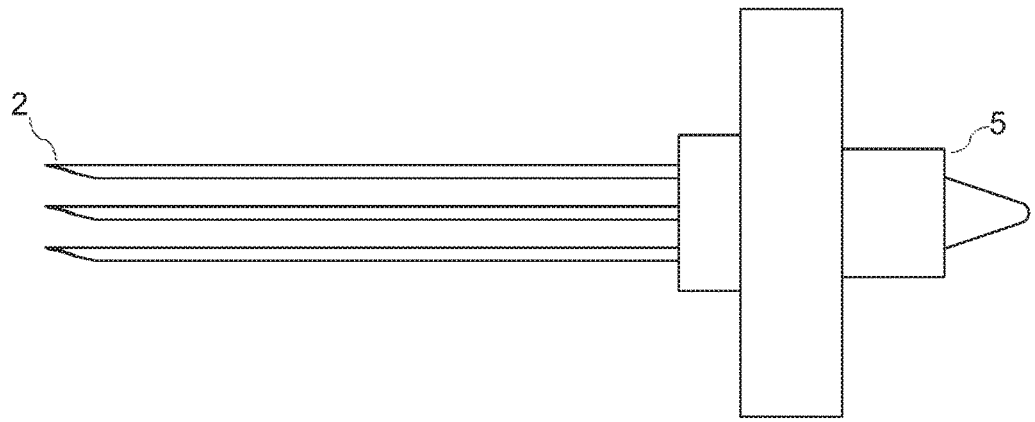
Figure 9C:
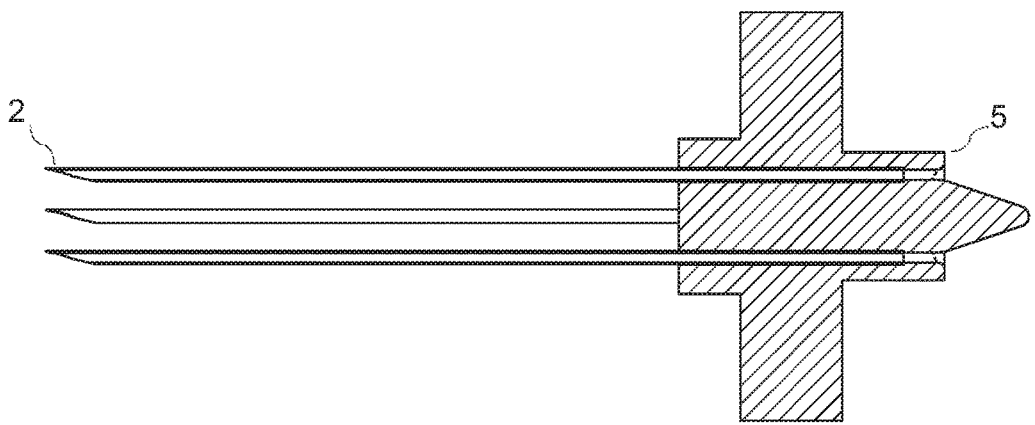

It should be appreciated that any size hub 5 may be selected to accommodate a plurality of needles. In the embodiments depicted in FIG. 6, the hub 5 may be as large as three (3) centimeters in diameter or as small as one-quarter (0.25) of a centimeter in diameter. Also, the needles may be secured into the hub by pressure as shown in FIG. 8A-8C or secured into the hub by glue as shown in FIG. 9A-9C.

Figure 6A:
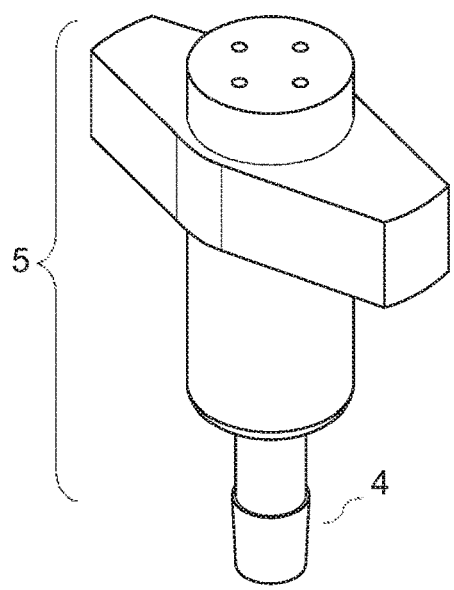
FIG. 6A-6D are views of an embodiment of the multiple injector needle apparatus. Independently.

Opposite the needle side of the hub 5 lies the second end 6 of the hub. The second end 6 is configured to receive IV tubing. In the example shown, butterfly IV tubing would connect to the second end 6. As shown in FIG. 6A, the hub 5 ideally would be made of plastic, and would have plastic handles 7 that would aid in the insertion of the needles into the injection port.

As shown in FIG. 4, the preferred embodiment of the apparatus has four 4.5 cm long 21 gauge needles 2 situated parallel precise placement into the silicone dome of the subcutaneous port during a tissue expansion procedure, thus increasing linear flow rate into the apparatus 1. In this embodiment, the actual diameter of the preferred embodiment of the hub 5 is approximately 5 millimeters. Tubing 4 attaches to hub 5 at second end 6 by stretching the tubing over the second end 6 of the hub. It should be appreciated that although the hub is shown as having a permanent connection to the tubing, it can be constructed such that the tubing is detachable. Tubing 4 terminates at the other end in a female connection of the leur lock base 3.

Figure 10:
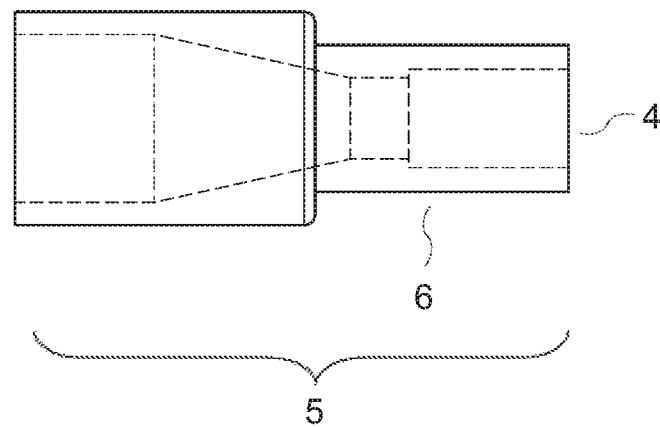
FIG. 10 is a cross sectional view of an embodiment of the hub of the apparatus.
Figure 11:
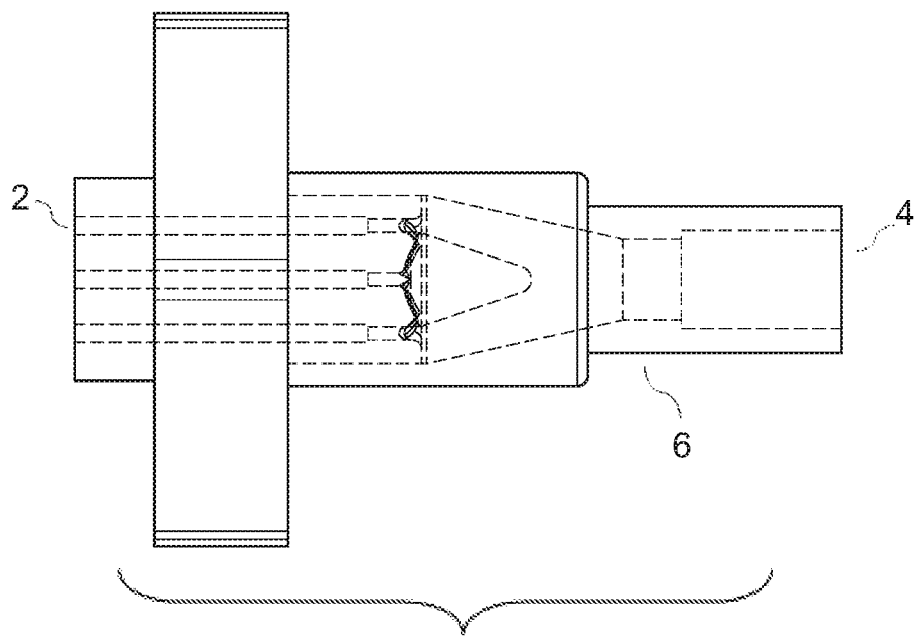
FIG. 11 is a cross sectional view of an embodiment of the hub of the apparatus with needles inserted.

As shown in FIG. 10, a potential embodiment of the tubing 4 connection to the hub 5 includes the entry portal for the tubing 4 having an inner diameter equal to the outer diameter of the tubing 4. The tubing 4 is securely attached to the second end 6 of the hub 5 allowing unimpeded fluid flow through the tubing 4 into the hub 5, as shown in FIG. 11.

To use the apparatus 1, leur lock base 3 is attached to a fluid source, such as a syringe. The fluid is then pushed through the tubing 4.

Figure 6B:
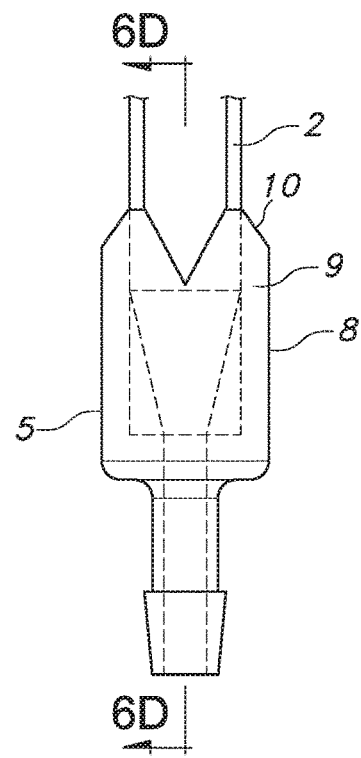
Figure 6C:
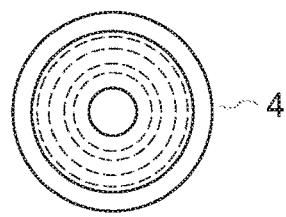
Figure 6D:
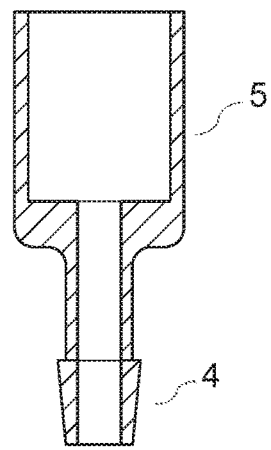

As shown in FIG. 6A-6D, the preferred embodiment of the apparatus 1 has a graded directing wall 8 with the narrowest portion at the fluid entry point (diameter of the tubing 4) and the widest portion at the fluid exit point (the plurality of needles 2) as pictured in FIG. 6B. As shown FIG. 6C, the gradual change in diameter of the system created by this angled directing wall 8 improves laminar flow.

As the fluid passes through the hub 5, it is distributed into the plurality of needles 2 via a directing cone 9. The directing cone 9 encourages and directs flow from the proximal end of the hub 5 into the needles 2. Without the directing cone 9, the fluid would require a 90 degree change in direction to enter the plurality of needles 2. Therefore, the increased directional flow in a graduated manner created by the directing cone 9 improves laminar flow, thus improving the actualized flow rate of the apparatus 1.

When the needles are filled with fluid, the needles are inserted into the injection port of the tissue expander, and the fluid the fills the tissue expander.

Potential embodiments of the needles 2 including a plurality of hypodermic needles, conical needles, taper needles or 1.5 inch needles where the diameter actually tapers from a larger gauge (i.e. 18 gauge) to a smaller 21 gauge size by point in the needle where the port puncture occurs, as the 21 gauge segment is required only for the portion that enters the port. Additionally, thin walled needles approaching six (6) times thinner that the standard needle wall are contemplated as an embodiment of the instant invention.

Another potential embodiment of the needles 2 includes ultra-thin wall 21 gauge needles that maintain the same external diameter of 0.81 millimeter, but a larger internal diameter.

As shown in FIG. 2, the preferred embodiment of the invention has a leur lock base 3 to allow for secure attachment of a syringe or other fluid source.

As shown in FIG. 2, the preferred embodiment of the invention consists of approximately 11 inches of IV tubing 4 to connect the needles. It should be appreciated, however, that the apparatus 1 can include any type or length of tubing 5 capable of connecting the needles 2.

As shown in FIG. 6B and FIG. 7C-7D, a potential embodiment of the invention consist of a cone-shaped cut out in the hub 5 that directs fluid flow from the base 3 into the needle 2 in a graduated manner. As shown in FIG. 7D, this aggregating cone 10 has a diameter equal to one half of the internal diameter of the hub 5 minus the diameter of the directing cone 9 (Formulaically: $D_{AC}=\frac{1}{2}(D_{hub}-D_{DC})$). Thus, surrounding each needle base, there is a graded wall, consisting of an internal gradual decrease in the diameter of the base leading to the needle, to channel fluid flow from the widest portion of the directing wall 8 to the base of the directing cone 9 and increase laminar flow rates.

Other potential embodiments of the IV tubing 4 include no rolling ball lock to stop IV flow; wider tubing to allow improved flow especially in the butterfly segment; a series of one-way valves instead of the four way stopcock to create a "no-touch" system allowing drawing and injecting into the port without manually turning the stocking into the correct position; and an autoinjector that prefills the syringe with a preset amount of saline (i.e. 35, 50, or 60 cc). The one-way valves would require two one-way valves allowing for inflow from the IV bag and out flow through the needle side, and the autoinjector could be created with a plastic handle and preloaded spring that draws back on the syringe to the desired level.

In another potential embodiment, the invention can be used in subcutaneous ports requiring high volume filling with fluid or fluidic suspension, such as in breast tissue and subcutaneous tumescence.

It should be appreciated that the invention can also have a fluid injection system including a series of valves, tubing, syringe and NaCL 0.9% IV fluid reservoir.

Figure 3:
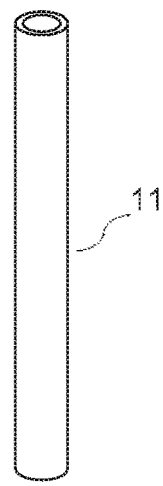
FIG. 3 is a front view of a plastic sleeve for needle protection.

As shown in FIG. 3, the apparatus 1 may include a plastic sleeve 11, to protect the needles 2 when not in use.

To demonstrate the efficiency of the instant invention compared to the current standard, we performed flow velocity measurements in a single-blind study as shown in Table 1. The measurements for the current standard were taken using a BRAUN brand 21 gauge winged needle infusion set 7B3050. The instant invention incorporated four 21 gauge hypodermic needles.

TABLE 1

Flow velocity data of the instant invention and the current standard reported as time to inject and the corresponding time savings of using the instant invention rather than the current standard.
Multiple Injector Needle vs. Braun 21 g Injector Data (in seconds)

| Simulation | Multiple Injector Needle - Time to Inject | Braun 21 g - Time to Inject | Time Savings |
|---|---|---|---|
| 1 | 6.600 | 25.500 | 18.900 |
| 2 | 7.000 | 29.000 | 22.000 |
| 3 | 6.900 | 27.800 | 20.900 |
| 4 | 6.800 | 26.800 | 20.000 |
| 5 | 6.900 | 25.500 | 18.600 |
| 6 | 7.100 | 27.200 | 20.100 |
| 7 | 6.200 | 26.500 | 20.300 |
| 8 | 6.300 | 27.300 | 21.000 |
| 9 | 6.800 | 28.400 | 21.600 |
| 10 | 6.500 | 28.200 | 21.700 |
| 11 | 5.300 | 22.600 | 17.300 |
| 12 | 5.400 | 24.300 | 18.900 |
| 13 | 5.700 | 23.900 | 18.200 |
| 14 | 5.300 | 23.100 | 17.800 |
| 15 | 5.400 | 24.400 | 19.000 |
| 16 | 5.200 | 23.900 | 18.700 |
| 17 | 5.500 | 24.500 | 19.000 |
| 18 | 5.300 | 23.800 | 18.500 |
| 19 | 6.100 | 23.600 | 17.500 |
| 20 | 5.200 | 24.200 | 19.000 |
| Ave. | 6.075 | 25.525 | 19.450 |
| Std. Dev. | 0.709 | 1.963 | 1.419 |

As shown in Table 1, the evaluation conducted showed that the multiple injector needle average flow rate is 4.2-fold greater than the BRAUN 21 g winged needle infusion set 7B3050. The average time for injection for twenty (20) trials wherein the apparatuses were filled with 60 cc of fluid was 6.075 seconds for the multiple injector needle, while the BRAUN 21 g standard took 25.525 seconds. The standard deviation for each apparatus was 0.71 and 1.96 seconds, respectively. The two-tailed P value for this evaluation was less than 0.0001, which, considered by conventional criteria, is an extremely statistically significant difference. Also, the mean of the multiple injector needle minus the current standard equals 19.450 seconds with a 95% confidence interval for this difference from 18.507 to 20.393. It should be appreciated that the instant invention using four needles results in greater than fourfold increase in injection rate.

Based on the results of this evaluation, the greater than four times increased flow velocity of the instant invention results in the tedious and painful injection process being much more comfortable to perform. With less force required for injection, less body bruising from pressing against the ribs or abdomen, and less thumb injury will result. For instance, the basal joint of the thumb sees a thirteen (13) times increased load from that created at the site of compression. If you press the syringe with your thumb with twenty (20) pounds per square inch of pressure, your thumb basal joint sees two hundred and sixty (260) pounds per square inch, decreasing the risk of the development of arthritis due to conducting such an injection. Most importantly, faster injection corresponds to faster surgery time with the patient under anesthesia for less time. Accordingly, patients will have better recovery periods, lower chances for infection, and likely faster discharge from the hospital due to the time savings provided by the instant invention.

Further, the faster process associated with the multiple injector needle will likely save total procedure time resulting in cost savings. For instance, in a bilateral reconstruction procedure, the faster process will likely save upwards of ten (10) minutes with moderate intraoperative fill volumes. This cost savings is quantified via a 2005 peer-reviewed study with average cost of $62.00 per minute. This cost does not include anesthesia costs, nor the expense of consumables. Thus, actual savings are even higher.

Also, as shown in Table 2, we measured fluid released from the port during injection to determine leakage of the instant invention.

TABLE 2

Leakage data of the multiple injector needle after being inserted and removed into the center of a port thirty (30) times
Leakage Data Log

| Day | Leak |
|---|---|
| 1-3 | No |
| 4-6 | No |
| 7-9 | No |
| 10-12 | No |
| 13-15 | No |
| 16-18 | No |
| 19-21 | No |
| 22-24 | No |
| 25-27 | No |
| 28-30 | No |
| 31-33 | No |
| 34-37 | No |
| 38-40 | No |
| 41-43 | No |
| 44-47 | No |
| 48-50 | No |
| 51-53 | No |
| 54-57 | No |
| 58-60 | No |
| 61-63 | No |
| 64-66 | No |
| 67-69 | No |
| 70-72 | No |
| 73-75 | No |
| 76-78 | No |
| 79-81 | No |
| 82-84 | No |
| 85-87 | No |

TABLE 2-continued

Leakage data of the multiple injector needle after being inserted and removed into the center of a port thirty (30) times
Leakage Data Log

| Day | Leak |
| --- | --- |
| 88-90 | No |
| 91-93 | N/A |

As shown in Table 2, no tissue expanders were found to be leaking following ninety (90) days of inspection. The multiple injector needle was used in three (3) different tissue expander samples (1 Mentor; 2 Allergan), and fluid was injected into the apparatus as well. The apparatus was turned upside down so that the port was at the lowest point and then wiped dry. Compression of the multiple injector needle with manual pressure was performed with the port at the lowest point in relationship to gravity. Visible and palpable testing was performed to look for any evidence of fluid released from the port. The lack of data leakage associated with the instant invention further indicates the reliability and efficiency of the design of the instant invention.

Although the invention has been described herein as being used with breast tissue expanders, it is contemplated that it can be used in any tissue expander or in any other device with an injection port that can accommodate multiple needles.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

I hereby claim:

1. A fluid injection device comprising:
a plurality of needles;
a hub having a first end portion, a second end portion, a plurality of needle bases at the second end portion, and a directing cone extending from the second end portion with the plurality of needle bases at least partially surrounding the directing cone, the directing cone tapering to a non-frustoconical tip in a direction away from the first end portion for diverting flow toward the plurality of needle bases, each of said plurality of needles being in fluid communication with a respective one of the plurality of needle bases and projecting from said first end portion of the hub; and
a base component, separate from and couplable to a second end portion of the hub, the non-frustoconical tip extending into a cavity of the base component, upstream of the plurality of needle bases, the base component comprising an inlet configured to receive tubing therein for connecting the device to a fluid source.

2. The device of claim 1, wherein said plurality of needles consists of at least two needles.

3. The device of claim 1, wherein said plurality of needles consists of four needles.

4. The device of claim 1, wherein said needles consist of hypodermic needles.

5. The device of claim 1, wherein said needles consist of 21 gauge needles.

6. The device of claim 1, wherein said needles are conical.

7. The device of claim 1, further comprising a base member coupled to the second end portion, wherein the base member is configured to be coupled to tubing having a terminal portion having a female luer lock base.

8. The device of claim 1, wherein said hub is made of plastic.

9. The device of claim 1, wherein said hub includes handles for enabling easier insertion of the needles into an injection port.

10. The device of claim 1, wherein said hub has graded walls surrounding the needle bases to increase laminar flow.

11. The device of claim 1, wherein said needles are ultra-thin wall needles, wherein the ultra-thin wall needles maintain the same external diameter as standard needles of the same size, but have a larger internal diameter than standard needles of the same size.

12. The device of claim 1, wherein said needles are configured to simultaneously enter an injection port of a tissue expander.

13. A fluid injection device comprising a hub and a base component, the hub having a first end portion, a second end portion, and a plurality of needle bases formed along said second end portion, said first end portion is configured to receive a plurality of needles to permit the plurality of needles to project from said first end portion of the hub, each of the plurality of needles being in fluid communication with a respective needle base, the hub further comprising a directing surface (i) being angled toward the needle bases and (ii) having a tapered shape that terminates in a non-frustoconical tip, the needle bases being arranged around the directing surface to promote laminar flow of a fluid along the directing surface toward the needle bases, the base component, separate from and couplable to a second end portion of the hub, the non-frustoconical tip extending into a cavity of the base component, upstream of the plurality of needle bases, the base component comprising an inlet configured to receive tubing therein for connecting the device to a fluid source.

14. A method of increasing fluid flow into an injection port of a tissue expander comprising the steps of:
   a. providing a hub and a base component coupled to a tubing attached to a fluid source, wherein said hub has a first end portion from which a plurality of needles project outward and a second end portion configured to receive fluid from the tubing, each of the plurality of needles being in fluid communication with a needle base formed along said second end portion, the hub further comprising a directing surface (i) being angled toward and at least partially surrounded by the needle bases and (ii) having a tapered shape that terminates in a non-frustoconical tip to promote laminar flow of a fluid toward the needle bases, the base component being separate from and couplable to a second end portion of the hub, the non-frustoconical tip extending into a cavity of the base component, upstream of the plurality of needle bases, the base component comprising an inlet configured to receive the tubing therein for connecting the hub to the fluid source; and
   b. pushing fluid through said tubing such that said fluid passes through the hub and into each of the plurality of needles.

15. The method of claim 14, further comprising: inserting said needles into a subcutaneous port.

16. The device of claim 13, wherein the directing surface comprises a directing cone.

17. The device of claim 13, wherein the directing surface comprises a directing wall.

18. The device of claim 13, wherein the plurality of needles are hypodermic needles.

19. The device of claim 1, wherein the plurality of needles are spaced no more than about 5 millimeters apart.

20. The device of claim 1, wherein the hub has a diameter in the range of about 0.25 cm to about 3 cm in diameter.

21. A multiple injector apparatus comprising a hub, a plurality of needle bases in the hub, a plurality of needles coupled to the hub and in fluid communication with the plurality of needle bases, a solid-core directing cone extending from the hub and tapering in direction away from the plurality of needle bases to a non-frustoconical tip for diverting flow toward the plurality of needle bases, and a base component, separate from and couplable to a second end portion of the hub, the non-frustoconical tip extending into a cavity of the base component, upstream of the plurality of needle bases, the base component comprising an inlet configured to receive tubing therein for connecting the apparatus to a fluid source.

22. The apparatus of claim 21, wherein the non-frustoconical tip is rounded.

23. The apparatus of claim 21, wherein the base component comprises a tubing connection section and a central section interposed between the tubing connection section and the cavity, at the tubing connection section having a first diameter, the central section comprising a second diameter, smaller than the first diameter.

24. The device of claim 1, wherein the non-frustoconical tip is rounded.

25. The device of claim 1, wherein the base component comprises a tubing connection section and a central section interposed between the tubing connection section and the cavity, at the tubing connection section having a first diameter, the central section comprising a second diameter, smaller than the first diameter.

26. The device of claim 13, wherein the non-frustoconical tip is rounded.

27. The device of claim 13, wherein the base component comprises a tubing connection section and a central section interposed between the tubing connection section and the cavity, at the tubing connection section having a first diameter, the central section comprising a second diameter, smaller than the first diameter.

28. The method of claim 14, wherein the non-frustoconical tip is rounded.

29. The method of claim 14, wherein the base component comprises a tubing connection section and a central section interposed between the tubing connection section and the cavity, at the tubing connection section having a first diameter, the central section comprising a second diameter, smaller than the first diameter.

* * * * *